US009188564B2

(12) United States Patent
Sulzer et al.

(10) Patent No.: US 9,188,564 B2
(45) Date of Patent: Nov. 17, 2015

(54) IONISATION METHOD FOR A UNIVERSAL GAS ANALYZER

(75) Inventors: Philipp Sulzer, Innsbruck (AT); Alfons Jordan, Sellrain (AT); Eugen Hartungen, Vols (AT); Tilmann Mark, Igls (AT)

(73) Assignee: Ionicon Analytik Gesellschaft M.B.H., Innsbruck (AT)

( * ) Notice: Subject to any disclaimer, the term of this patent is extended or adjusted under 35 U.S.C. 154(b) by 275 days.

(21) Appl. No.: 13/261,590

(22) PCT Filed: Aug. 17, 2011

(86) PCT No.: PCT/EP2011/064170
§ 371 (c)(1),
(2), (4) Date: Jun. 17, 2013

(87) PCT Pub. No.: WO2012/022772
PCT Pub. Date: Feb. 23, 2012

(65) Prior Publication Data
US 2013/0260473 A1    Oct. 3, 2013

(30) Foreign Application Priority Data
Aug. 18, 2010  (EP) .................................. 10173224

(51) Int. Cl.
*G01N 24/00* (2006.01)
*G01N 27/62* (2006.01)
*H01J 49/14* (2006.01)

(52) U.S. Cl.
CPC .............. *G01N 27/62* (2013.01); *H01J 49/145* (2013.01); *Y10T 436/24* (2015.01)

(58) Field of Classification Search
None
See application file for complete search history.

(56) References Cited

U.S. PATENT DOCUMENTS

| 4,975,576 A | 12/1990 | Federer et al. | |
| 2007/0102634 A1 | 5/2007 | Frey et al. | 250/288 |

FOREIGN PATENT DOCUMENTS

| DE | 19549144 A1 | 7/1996 | ............ H01J 49/10 |
| WO | 0165250 A1 | 9/2001 | |
| WO | 2009/048739 A2 | 4/2009 | ............ H01J 49/10 |

OTHER PUBLICATIONS

Hansel, A. et al. Proton transfer reaction mass spectrometry: on-line trace gas analysis at the ppb level, 1995, International Journal of Mass Spectrometry and Ion Processes, vol. 149/150, pp. 609-619.*

(Continued)

*Primary Examiner* — Robert Xu
(74) *Attorney, Agent, or Firm* — Ohlandt, Greeley, Ruggiero & Perle, L.L.P.

(57) ABSTRACT

The invention provides a method and system for analyzing a gas for the presence of a reactant compound via reaction of primary ions of a specific type. A source gas is introduced to a reaction chamber and ionized in this chamber. The pressure in the reaction chamber is adjusted to avoid the formation of protonated species and other impurities. The primary ions generated in the reaction chamber are transferred to a drift tube. The gas to be analyzed is diluted with a carrier gas and the resulting mixture is introduced into the drift tube. The ionization energy of the carrier gas is equal to or higher than the ionization energy of the primary ions. The product ions resulting in the drift tube from a reaction of the primary ions with the reactant present in the gas to be analyzed are then detected, for example using a mass spectrometer. Preferably, an existing PTR-MS setup is used to perform the method of the present invention.

8 Claims, 2 Drawing Sheets

(56) References Cited

OTHER PUBLICATIONS

A. Jordan et al., Int'l J. Mass Spec. 286 (2009) 32-38.

Third Party Observation from the European Patent Office from corresponding EP20110751580 dated Mar. 31, 2014 (3 Pages).

"Proton transfer reaction mass spectrometry on-line trace gas analysis at the ppb level" 1995 (International Journal of Mass Spectrometry and Ion Processes pp. 149/150 (1995)).

"Chemical Ionisation by Ion-Molecule Reaction" Kore Technology Limited 2006 from https://web.archive.org/web/20060716115858/http://www.kore.co.uk/cireact.htm.

Lagg, A. et al. "Applications of proton transfer reactions to gas analysis" 1995 (International Journal of Mass Spectrometry and Ion Processes vol. 134, No. 1, Jun. 9, 1994, pp. 55-66, Elsevier Scientific Publishing Co., Amsterdam, Netherlands).

Office Action from the European Patent Office for European Patent Application No. 11 751 580.9-1803 dated Jun. 23, 2014 (8 Pages).

\* cited by examiner

IONISATION METHOD FOR A UNIVERSAL GAS ANALYZER

This Patent Application is a US National Phase Patent Application from PCT Application No. PCT/EP2011/0064170, filed Aug. 17, 2011 and claiming priority from EP Patent Application No. 10173224.6 filed Aug. 18, 2010.

FIELD OF THE INVENTION

The present invention relates to a method for analyzing a gas for detecting the presence of a reactant compound with help of ions of a specific type, in particular using proton-transfer-reaction mass spectrometry (PTR-MS).

BACKGROUND TO THE INVENTION

In PTR-MS, as described, for example, in DE-A-195 49 144, a highly pure ion current which is substantially comprised of $H_3O^+$ ions is used for a chemical reaction with certain constituents of a sample gas through proton transfer reactions, in order to analyze subsequently the ions formed in the sample gas by means of mass spectrometry. To provide the ion current, $H_2O$ vapour is ionized in a first ionization region (via a hollow cathode discharge), thereby forming various ions, such as $O^+$, $OH^+$, $H^+$, $H_2^+$, etc. Using a weak electric field, these ions are transferred to a second region. In the second region, the ions react with $H_2O$ present mainly through the following reactions:

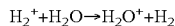

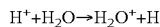

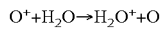

and finally

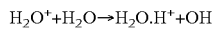

The reactions in the two regions thus finally lead predominantly to the production of $H_3O^+$ ions. In order to avoid $H_3O^+.(H_2O)_N$ cluster ions, that may be formed through association reactions in successive collisions with neutral collision partners, the ions may be guided through an appropriate electric field that ensures that these cluster ions have sufficient kinetic energy so that the collisions are primarily dissociative. A drift tube may be used to apply the necessary energy to the clusters. In this way, a highly pure stream of $H_3O^+$ ions is achieved. Further means may be applied to decrease the amount of these cluster ions.

Also other ions may be produced using this method. For example, A. Jordan et al. demonstrated in Int. J. Mass. Spec. 286 (2009) 32-38 that a similar, slightly modified setup may also be used to generate highly pure $NO^+$ and $O_2^+$ ions, respectively. In EP-A-1 566 829, some additional examples for possible reacting ions are given. With regard to the prior art, reference is further made to WO 2009/048739 A2 and U.S. 2007/102634 A1.

In order to analyze a sample gas by reaction with the primary ions, e.g. $H_3O^+$ ions, the sample gas is introduced into a drift tube reactor. For example, the drift tube may be connected to the outside for analyzing the surrounding air. Also, the drift tube may include an input port for introducing a sample gas into this drift tube. In the drift tube, depending on the type of primary ions used, either proton transfer, charge transfer or association reactions take place. However, no matter which type of primary ion is utilized, it is absolutely necessary that the primary ions only interact with the substances that are to be detected which are present in small traces compared to the carrier gas in the drift tube. For example, in case $H_3O^+$ is used, where a proton transfer only takes place for molecules having a higher proton affinity than water, the common constituents of air ($N_2$, $O_2$, CO, $CO_2$, etc. with proton affinities lower than that of water) do not react with the primary ions. In this way, only the small amounts of impurities (having proton affinities higher than that of water) in the air will undergo proton transfer. This is also true for every other protonated primary ion having a higher proton affinity than common air compounds. In case charge transfer ionization is used, the ionization energy of the primary ion has to be lower than the ionization energy for common air compounds, if this is used as sample gas to be analyzed.

The product ions that are formed either via proton, via charge transfer or other ion molecule reactions can be analyzed by any type of mass spectrometer, for example those using quadrupoles or time-of-flight analyzers.

However, due to the limitations referred to above, it is not possible to use primary ions in a PTR-MS setup that allow to ionize (and thus detect) for instance substances with properties (proton affinities, ionization energies) similar to common air compounds. If, for example, a primary ion is used that would allow to chemically ionize $N_2$, the majority of primary ions would react with this dominating compound of air and insufficient reagent ions would be available for the trace compounds, i.e. the reactant that is to be analyzed. As a consequence, important substance classes in common air, for example many traffic exhaust products like CO, $NO_x$, etc., cannot be analyzed in a conventional PTR-MS setup.

There is therefore a need to provide a method and system capable for universal gas analysis. In particular, it would be desirable to provide a method that is capable for universal gas analysis in a PTR-MS setup, in particular without the limitation for molecules to be analyzed having a higher proton affinity (for proton transfer) or lower ionization energy (for charge transfer) than common air compounds.

SUMMARY OF THE INVENTION

The present invention therefore provides a method and system for analyzing a gas for the presence of a reactant compound via reaction of primary ions of a specific type, as defined according to the claims. According to the method of the present invention, a source gas, preferably but not limited to noble gases, in particular Kr, Xe, Ne, Ar, He, is introduced to and ionized in a reaction chamber (e.g. a hollow cathode discharge). The source gas is introduced to the reaction chamber with a flow rate that generally depends on the individual setup and is typically between 0.5 and 10 sccm ("standard cubic centimeters per minute", i.e. $cm^3$/min at standard conditions). The pressure in the reaction chamber is adjusted to avoid the formation of protonated species (due to reactions with background impurities) and other minor secondary ions. The pressure in the reaction chamber may, for example, be between 0.4 and 1 hPa. The primary ions generated in the reaction chamber are then transferred to a drift tube. The gas that is to be analyzed is introduced into the drift tube, wherein this gas (to be analyzed) is diluted with a carrier gas prior to the supply to the drift tube. The ionization energy of the carrier gas has to be higher than the ionization energy of the primary ions. As an exception to this rule it is possible to use the source gas that has been used for generating the primary ions as the carrier gas (i.e. the ionization energies are equal). The dilution rate of the gas to be analyzed with the carrier gas depends on the primary ion yield and the setup, and may be between 1:5 to 1:1000. The product ions resulting from a reaction of the primary ions with the reactant present in the gas to be analyzed are then detected, for example using a mass spectrometer.

An existing PTR-MS setup may be used to perform the method of the present invention. Specifically, the two ionization chambers present in a PTR-MS setup may be used to ionize the source gas as follows. The source gas is introduced to the first ionization chamber of the PTR-MS setup wherein the source gas is ionized. The ionized gas is then transferred to the second ionization chamber of the PTR-MS setup. Adjusting the pressure to avoid the formation of e.g. protonated species is primarily performed in the second ionization chamber. This may be achieved by opening a valve situated between the second ionization chamber and the pumping system which may be installed in a known PTR-MS setup. Accordingly, the first and second ionization chambers of the known PTR-MS setup may be used in combination to perform the steps of introducing and ionizing the source gas, and adjusting the pressure according to the method of the present invention.

The invention further provides a device for analyzing a gas for the presence of a reactant using the method of the present invention. The device comprises a reaction chamber connected to a drift tube. The reaction chamber comprises an inlet for introducing a source gas, means for ionizing the source gas, for example, a plasma reactor, and means for adjusting the pressure in the reaction chamber. The drift tube includes an inlet for introducing a mixture of the gas to be analyzed and a carrier gas. The device may include mixing means for diluting the gas to be analyzed with the carrier gas. Furthermore, the device comprises detection means, for example a mass spectrometer, connected to the output of the drift tube.

With the method and the system of the present invention, it is possible to additionally analyze substances having a similar or lower proton affinity and/or a similar or higher ionization energy than common air compounds. The method of the present invention may advantageously be performed in existing PTR-MS setups.

BRIEF DESCRIPTION OF THE DRAWINGS

The present invention will be described in more detail with reference to the Figures, wherein FIG. 1 schematically illustrates a device according to an embodiment of the present invention

DETAILED DESCRIPTION OF THE INVENTION

Figure 1:
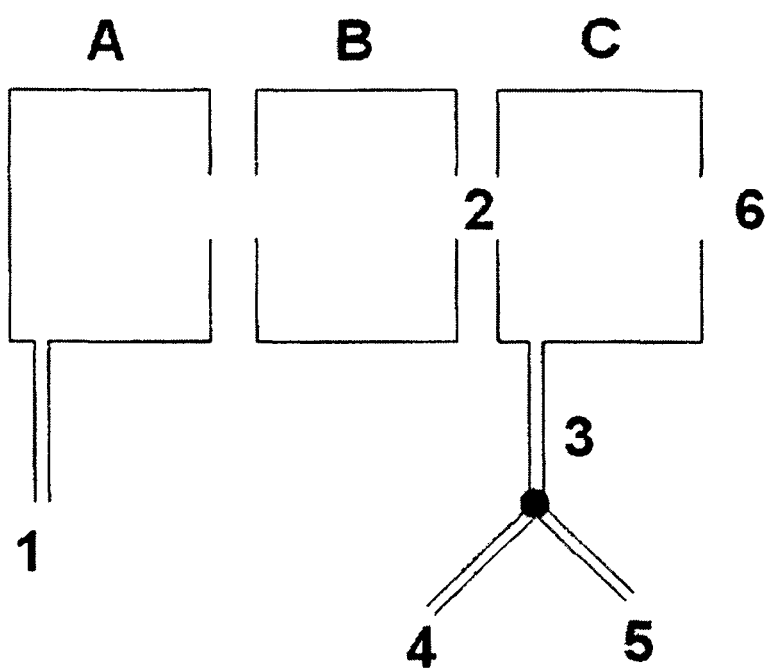

FIG. 1 schematically shows a device that is adapted to perform the analysis method according to an embodiment of the present invention. The device shown in FIG. 1 is similar to a known PTR-MS setup and comprises a first ionization chamber A, a second ionization chamber B and a drift tube C. Source gas is introduced through input port 1 to the first ionization chamber A. For example, a gas cylinder containing the substance to be used as primary ions may be connected at port 1. Possible gases are preferably, but not limited to, noble gases, for example, Kr, Xe, Ne, Ar, He, etc. Gas flow rates are strongly depending on the individual setup but are typically between 0.5 and 10 sccm. In ionization chamber A, the source gas is ionized using suitable means (not shown). For example, a plasma reactor may be arranged in chamber A, e.g. the burning plasma of a hollow cathode discharge partially ionizing the source gas.

The ions generated in the first ionization chamber A are then transferred to the second ionization chamber B. In a previously known PTR-MS method, the pressure in the second ionization chamber B must be high enough to ensure a sufficient number of collisions between the compounds coming from the first ionization chamber A. This is particularly important for a highly pure primary ion yield of protonated water ions, that is achieved as explained above in conjunction with the prior art.

In contrast thereto, the pressure in the second ionization chamber B according to the present invention is strongly reduced to limit the number of collisions when using non-protonated primary ions (e.g. $Kr^+$, $Xe^+$, $Ne^+$, $Ar^+$, $He^+$, etc.), to avoid the formation of a protonated species (e.g. $KrH^+$) originating from reactions with impurities or the production of dimer ions (e.g. $Kr_2^+$). This may be achieved by increasing the pumping speed at the end of the second ionization chamber B, i.e. at the orifice (pumped ring) 2 connecting the second ionization chamber and the drift tube C, to a level where collisions are reduced and the pressure is still high enough to suppress or at least keep low back flow of gas from drift tube C. This can be achieved, for example, by installing a pumping line and valve between the pumping system and the orifice 2 or using a valve which already is installed in some existing PTR-MS setups. When using the PTR-MS device in the known proton-transfer-mode according to the prior art, the valve must be nearly closed. In contrast thereto, the valve should be almost opened in the charge-transfer-mode used according to the present invention.

In the description above, the use of an existing PTR-MS setup was exemplary shown with reference to FIG. 1. However, also a modified setup may be used. For example, it is possible to perform the steps of introducing and ionizing the source gas and adjusting the pressure in only one ionization chamber that is directly connected to the drift tube.

For the type of primary ions that are preferably used according to the present invention, the sample air that has to be analyzed must not be introduced directly into the drift tube, but has to be diluted with some carrier gas (e.g. $N_2$, Ar, He, etc. or the same gas as it is used for generating the primary ions) prior to introduction. It is very important that the carrier gas possesses a higher ionization energy than the primary ion or that the same gas is used for source and carrier gas. The dilution rate depends on the primary ion yield and the setup, and can be, but is not limited to, a rate of 1:5 up to 1:1000. FIG. 1 shows an inlet 4 for the carrier gas and an inlet 5 for the gas to be analyzed. Mixing means 3 are provided at the inlet to the drift tube to perform the dilution. Alternatively, the dilution may already be done in a container holding the sample, for example, gas cylinders with trace compounds mixed in a gas having a higher ionization energy than the primary ion.

The product ions resulting in the drift tube from the reaction of the primary ions with the reactant present in the gas to be analyzed are then fed via an opening 6 to a detector, e.g. a mass spectrometer (not shown) for detecting the presence and the amount of said product ions.

With this setup, all primary ions up to the ionization energy of He (24.59 eV) can be utilized when using the appropriate carrier gas and therefore nearly all existing molecules can be ionized by charge transfer. In particular, by diluting the gas to be analyzed with a carrier gas, it is possible to also use primary ions that have an ionization energy higher than the ionization energy of common air compounds, in particular $N_2$. That is, the present invention dramatically increases the possible fields of application of a PTR-MS instrument, while preserving the specific advantages of this method.

Figure 2:
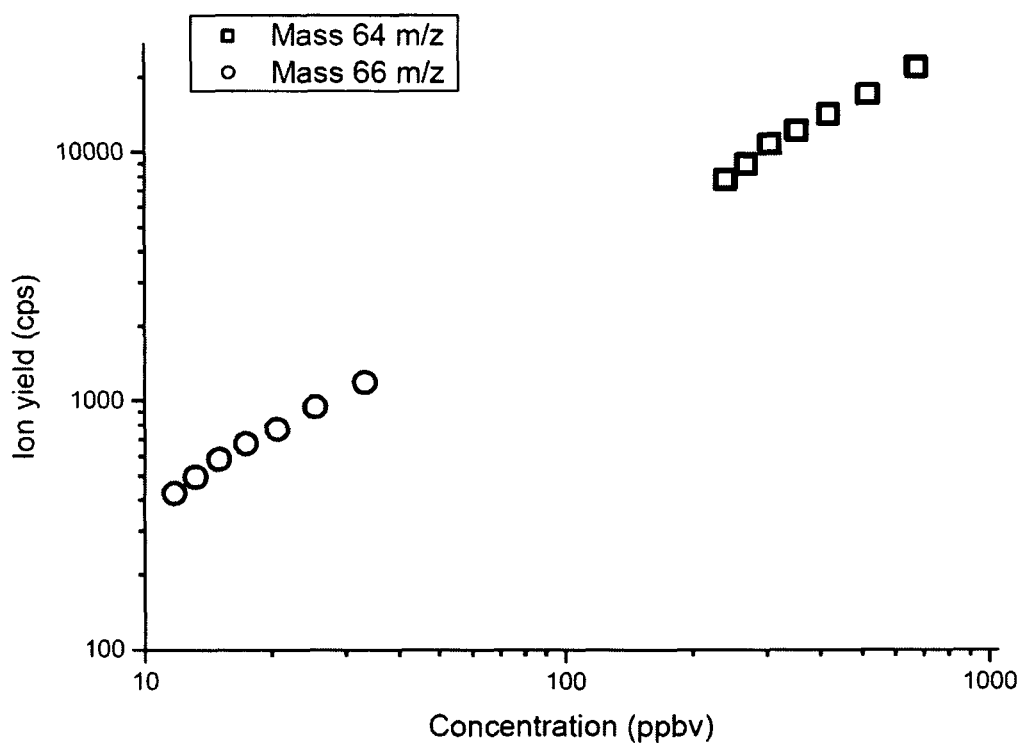
FIG. 2 shows the result of a measurement of $SO_2$ diluted with argon carrier gas and using $Kr^+$ ions as ionizing species.

FIG. 2 illustrates example measurements performed with the method according to the present invention. In the example shown in FIG. 2, $SO_2$ having an ionization energy of 12.3 eV was measured using $Kr^+$ ions as primary ions that have an ionization energy of 14 eV. Ar was used as a carrier gas. The sample gas consisted of 975 ppbv $SO_2$ in $N_2$ (ionization energy 15.59 eV) and was diluted with Ar (ionization energy 15.76 eV; i.e. ionization energies of Ar and $N_2$ are higher than that of Kr) to the stated amounts. FIG. 2 shows the results of $SO_2$ molecules detected at mass 64 m/z and its isotope at mass 66 m/z which is present in the natural ratio of 5%. In the exemplary measurement shown in FIG. 2, the Kr flow rate to the first ionization chamber was 1 sccm, while the pressure in the second ionization chamber was 0.6 hPa. Moreover, it can be seen that the ion yield measured for different concentrations of the reactant compound in the sample gas is (as in case of ordinary PTR-MS usage) linearly depending on these concentrations; this allows simple absolute calibrations for the whole range of concentrations.

The invention claimed is:

1. Method for analyzing a gas for the presence of a reactant compound by reaction with primary ions of a specific type, the method comprising the steps of
   (a) introducing a source gas to a reaction chamber and ionizing the source gas to yield primary ions, wherein the pressure in the reaction chamber is adjusted to avoid the formation of protonated species and other parasitic ions;
   (b) transferring the primary ions to a drift tube;
   (c) diluting the gas to be analyzed with a carrier gas and introducing the diluted gas into the drift tube, wherein the ionization energy of the carrier gas is equal to or higher than the ionization energy of the primary ions; and
   (d) detecting the presence of product ions resulting from a reaction of the primary ions with the reactant.

2. Method according to claim 1 wherein the primary ions are noble gas ions selected from the group consisting of $Kr^+$, $Xe^+$, $Ne^+$, $Ar^+$, and $He^+$.

3. Method according to claim 1, wherein the flow rate of the source gas to the reaction chamber is between 0.5 and 10 sccm.

4. Method according to claim 1, wherein the pressure in the reaction chamber is between 0.4 and 1 hPa.

5. Method according to claim 1, wherein the reaction chamber comprises a first and a second ionization chamber (A, B), wherein step (a) comprises the steps of
   (a1) introducing the source gas to the first ionization chamber (A) and ionizing the source gas;
   (a2) transferring the ionized source gas to the second ionization chamber (B), wherein the pressure in the second ionization chamber (B) is adjusted to avoid the formation of a protonated species and other parasitic ions.

6. Method according to claim 1, wherein the source gas that has been used for generating the primary ions is also used as the carrier gas.

7. Method according to claim 1, wherein the dilution rate of the gas to be analyzed and the carrier gas is between 1:5 and 1:1000.

8. Method according to claim 1, wherein the step of diluting comprises a step of mixing the gas to be analyzed with the carrier gas.

* * * * *